United States Patent
DiFoggio

(10) Patent No.: US 9,110,182 B2
(45) Date of Patent: Aug. 18, 2015

(54) GASEOUS GRAVIMETER

(75) Inventor: Rocco DiFoggio, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 650 days.

(21) Appl. No.: 13/455,251

(22) Filed: Apr. 25, 2012

(65) Prior Publication Data

US 2013/0283888 A1 Oct. 31, 2013

(51) Int. Cl.
- *G01N 9/00* (2006.01)
- *G01V 7/04* (2006.01)
- *G01N 9/36* (2006.01)
- *G01V 7/16* (2006.01)

(52) U.S. Cl.
CPC .. *G01V 7/04* (2013.01); *G01N 9/36* (2013.01); *G01V 7/16* (2013.01)

(58) Field of Classification Search
USPC .................. 73/382 G, 382 R, 30.04
See application file for complete search history.

(56) References Cited

U.S. PATENT DOCUMENTS

| 5,290,846 A | 3/1994 | Tuminello |
| 6,014,895 A | 1/2000 | Vail, III |
| 6,450,028 B1* | 9/2002 | Vail, III ............... 73/382 G |
| 2009/0114013 A1* | 5/2009 | DiFoggio .............. 73/382 R |

OTHER PUBLICATIONS

Paul Melchoir, (2009), Gravimetric Measuring Techniques, in Physical Methods, Instruments, and Measurements, vol. II, pp. 259-289, [Ed. Yuri M. Tsipenyuk], in Encyclopedia of Life Support Systems (EOLSS), Developed under the Auspices of the UNESCO, Eolss Publishers, Oxford, UK, {http://www.eolss.net}.

* cited by examiner

*Primary Examiner* — Hezron E Williams
*Assistant Examiner* — Xin Zhong
(74) *Attorney, Agent, or Firm* — Cantor Colburn LLP

(57) ABSTRACT

An apparatus for estimating gravitational acceleration includes: a chamber having a longitudinal axis and configured to contain a first gas; a first cavity ring-down spectrometer configured to measure a density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis; and a processor configured to receive a first density measurement from the first cavity ring-down spectrometer and to estimate the gravitational acceleration using the first density measurement.

22 Claims, 5 Drawing Sheets

GASEOUS GRAVIMETER

BACKGROUND

Geologic formations are used for many purposes such as hydrocarbon production, geothermal production, and carbon dioxide sequestration. Boreholes are typically drilled into the formations in order to access the formations and perform measurements associated with a proposed use of the formations. One type of measurement is gravity.

Gravity measurements can provide different types of information. Gravity measurements sense far beyond the wellbore s they minimize the effects of the near wellbore environment such as the presence of metal well casing or of fluid invasion, which can significantly alter or block the response of traditional logging tools. Gravity measurements made at two depths can provide the average formation density between those two depths. The average formation density depends not only on the rock type and its porosity but on the fluid that fills the pores of the rock. Gravity measurements that are repeated over time, either in the wellbore or on the surface (often called a "4-D survey"), can allow one to do reservoir monitoring and to observe when water from a water flood has replaced oil or when a gas cap has enlarged as the oil below it was produced. Gravity measurements can be used in old wells through casing to find gas zones that were considered uneconomic at the time the well was drilled. Gravity measurements can also be used in washed out, rugose, or fractured zones, and where the formation was damaged or oxidized.

Another type of information is related to obtaining the true vertical depth of the gravimeter that is measuring gravity in a borehole if one knows, or can estimate, the average formation density from the surface to the gravimeter. As boreholes become deviated from the vertical, it is more difficult to account for the deviation due to wireline stretch or drill pipe bending in estimating true vertical depth. As gravitational acceleration is a function of depth in a formation, the true vertical depth can be determined at any point in a borehole from gravity measurements. Hence, it would be well appreciated in the petroleum industry to develop improved gravimeters and to increase the accuracy of gravity measurements.

BRIEF SUMMARY

Disclosed is an apparatus for estimating gravitational acceleration. The apparatus includes: a chamber having a longitudinal axis and configured to contain a first gas; a first cavity ring-down spectrometer configured to measure a density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis; and a processor configured to receive a first density measurement from the first cavity ring-down spectrometer and to estimate the gravitational acceleration using the first density measurement.

Also disclosed is an apparatus for estimating gravitational acceleration under a surface of the earth. The apparatus includes: a carrier configured to be conveyed through a borehole penetrating the earth; a chamber disposed at the carrier and configured to contain a first gas, the chamber having a longitudinal axis; a first cavity ring-down spectrometer configured to measure a density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis; and a processor configured to receive a first density measurement from the first cavity ring-down spectrometer and to estimate the gravitational acceleration using the first density measurement.

Further disclosed is a method for estimating gravitational acceleration. The method includes: measuring a density of a first gas disposed in a chamber having a longitudinal axis using a first cavity ring-down spectrometer configured to measure the density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis; and estimating the gravitational acceleration using a processor configured to estimate the gravitational acceleration using the first density measurement as input.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the Figures.

Figure 1:
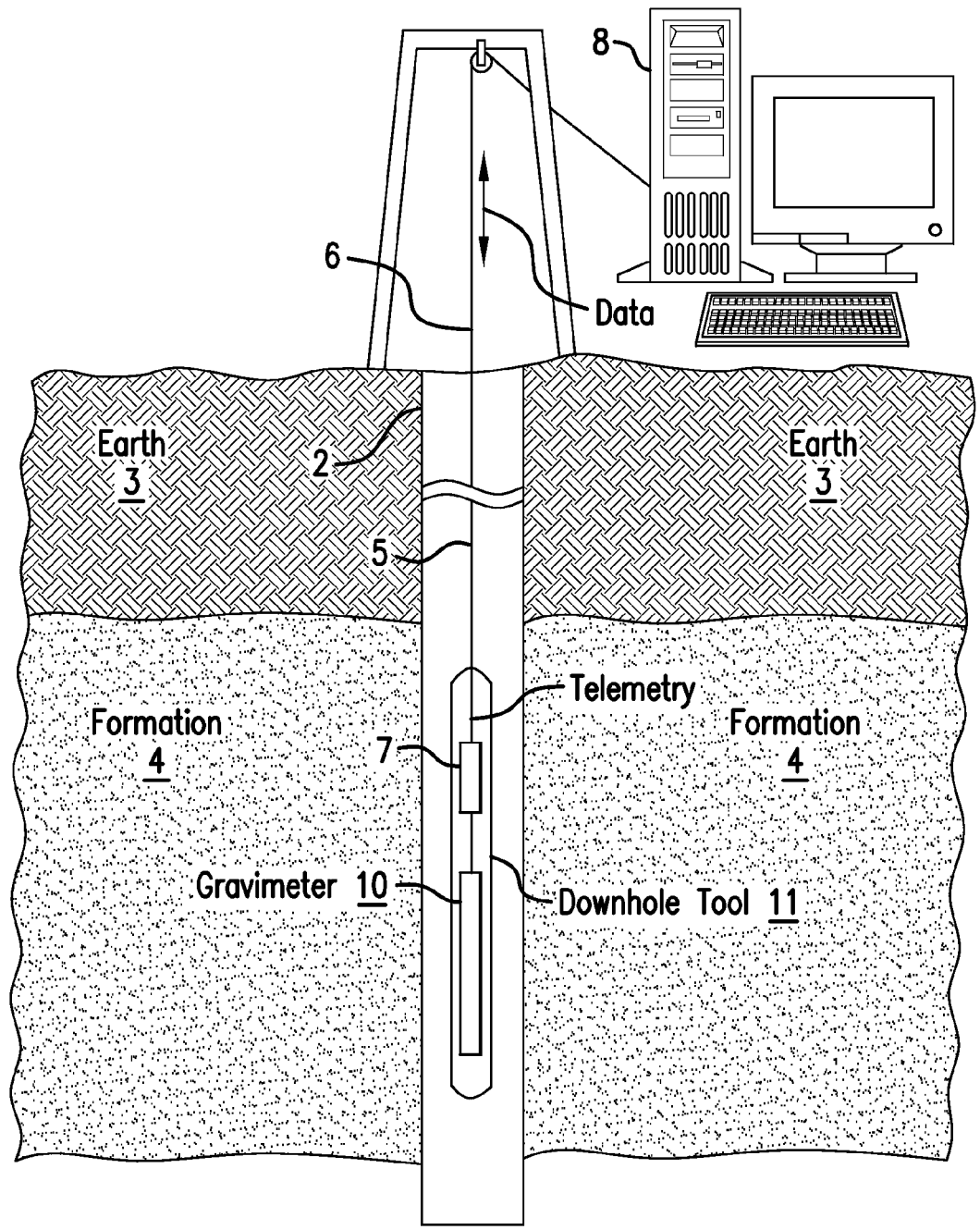
FIG. 1 illustrates an exemplary embodiment of a gravimeter disposed in a borehole penetrating the earth.

FIG. 1 illustrates a cross-sectional view of an exemplary embodiment of a downhole tool 11 having a gravimeter 10 disposed in a borehole 2 penetrating the earth 3, which includes an earth formation 4. The downhole tool 11 is conveyed through the borehole 2 by a carrier 5. In the embodiment of FIG. 1, the carrier 5 is an armored wireline 6. Besides supporting the downhole tool 11 in the borehole 2, the wireline 6 can also provide communications between the downhole tool 11 and a computer processing system 8 disposed at the surface of the earth 3. In logging-while-drilling (LWD) or measurement-while-drilling (MWD) embodiments, the carrier 5 can be a drill string or drill tubular. In order to operate the gravimeter 10, process gravimeter measurements, and/or provide a communications interface with the surface computer processing system 8, the downhole tool 11 includes downhole electronics 7. Processing functions including data recordation can be performed by the downhole electronics 7, the surface processing system 8, or a combination thereof.

The gravimeter 10 is an instrument configured to measure a value of gravity or gravitational acceleration where the gravimeter 10 is located. While FIG. 1 illustrates one embodiment of the gravimeter 10 configured for borehole applications, the gravimeter 10 can also be used to measure gravity at non-borehole locations, such as at or above the surface of the earth 3 or in marine applications.

Figure 2:
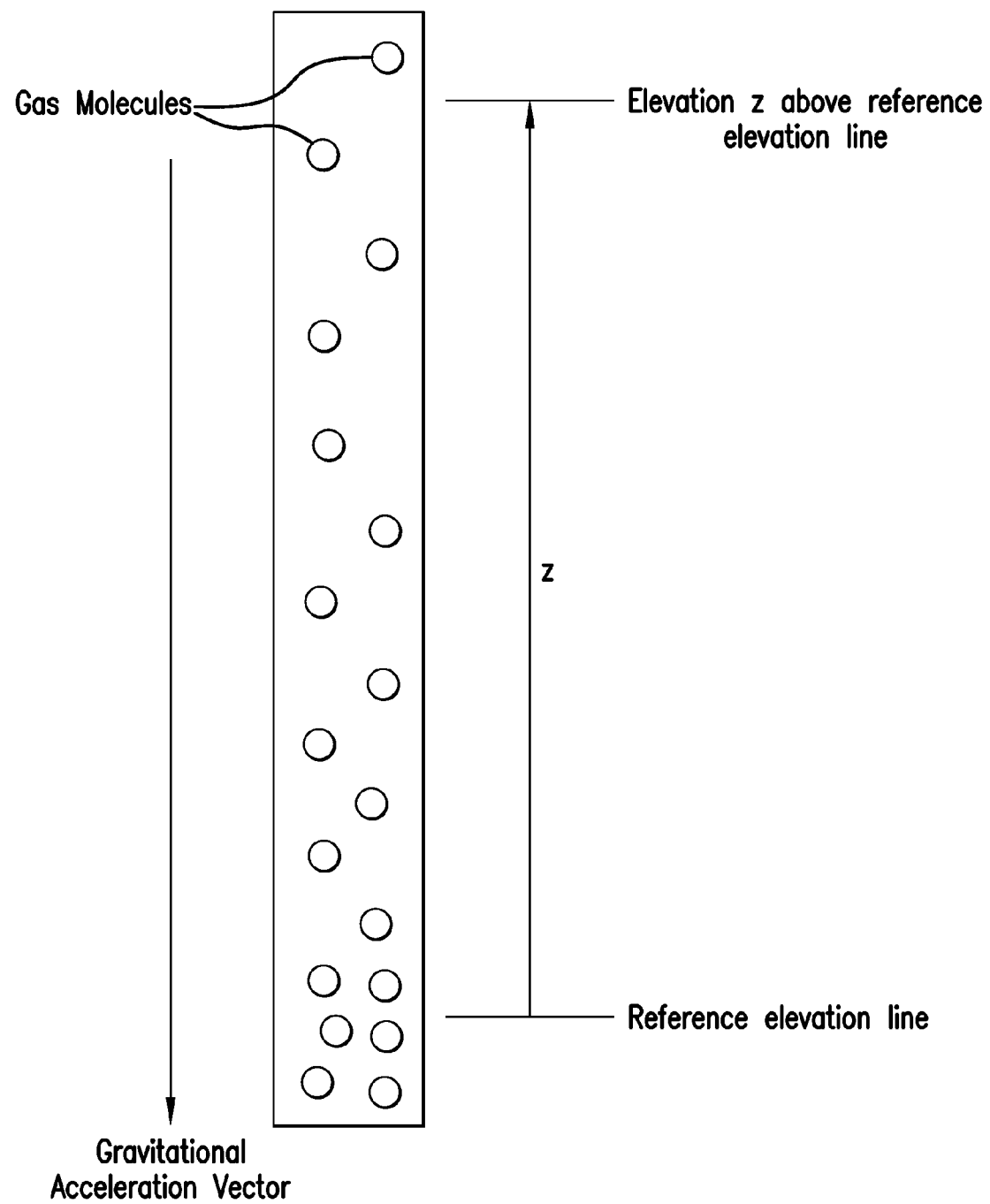
FIG. 2 depicts physical aspects of measuring gravity with a column of gas.

The gravimeter 10 is based on the principle that a vertical column of gas as illustrated in FIG. 2 will have a higher density at the bottom of the column than at the top due to the force of gravity acting down on the gas in the chamber. If the column of gas is in a zero-gravity environment, the density of the gas would be the same throughout the column. The Boltzmann energy distribution, which accounts for kinetic energy and potential energy due to gravity, can be used to relate the gravitational acceleration acting on a gas to the density of the gas. Equation (1) represents the probability P that a gas molecule will be at elevation z above a reference elevation with respect to the probability that the gas molecule will be at the reference elevation.

$$P = (1 - e^{-\{Mgz/kT\}}) \quad (1)$$

where M is the mass of the gas molecule, g is the gravitational acceleration acting on the gas molecule, z is the height of the gas molecule above a reference elevation, k is the Boltzmann constant, and T is the absolute temperature of the gas molecule. For example, if P is 0.998, then the gas molecule is 1/0.998 times more likely to be at the reference elevation than at elevation z. In other words, the gas density at elevation z is only 99.8% of the gas density at elevation zero (i.e., reference elevation), which is approximately the density variation of gaseous perfluorodecalin per meter of gas column. Therefore, in one or more embodiments by knowing T, M, z, and the ratio of gas density at elevation z to gas density at the reference elevation, g can be calculated. It can be appreciated from Equation (1) that it is important to keep the temperature T constant when making density measurements or to account for temperature changes. A second gas, which is lightweight, helps to even out any temperature differences in the chamber because the thermal conductivity of a gas increases as its molecular weight decreases.

Figure 3:
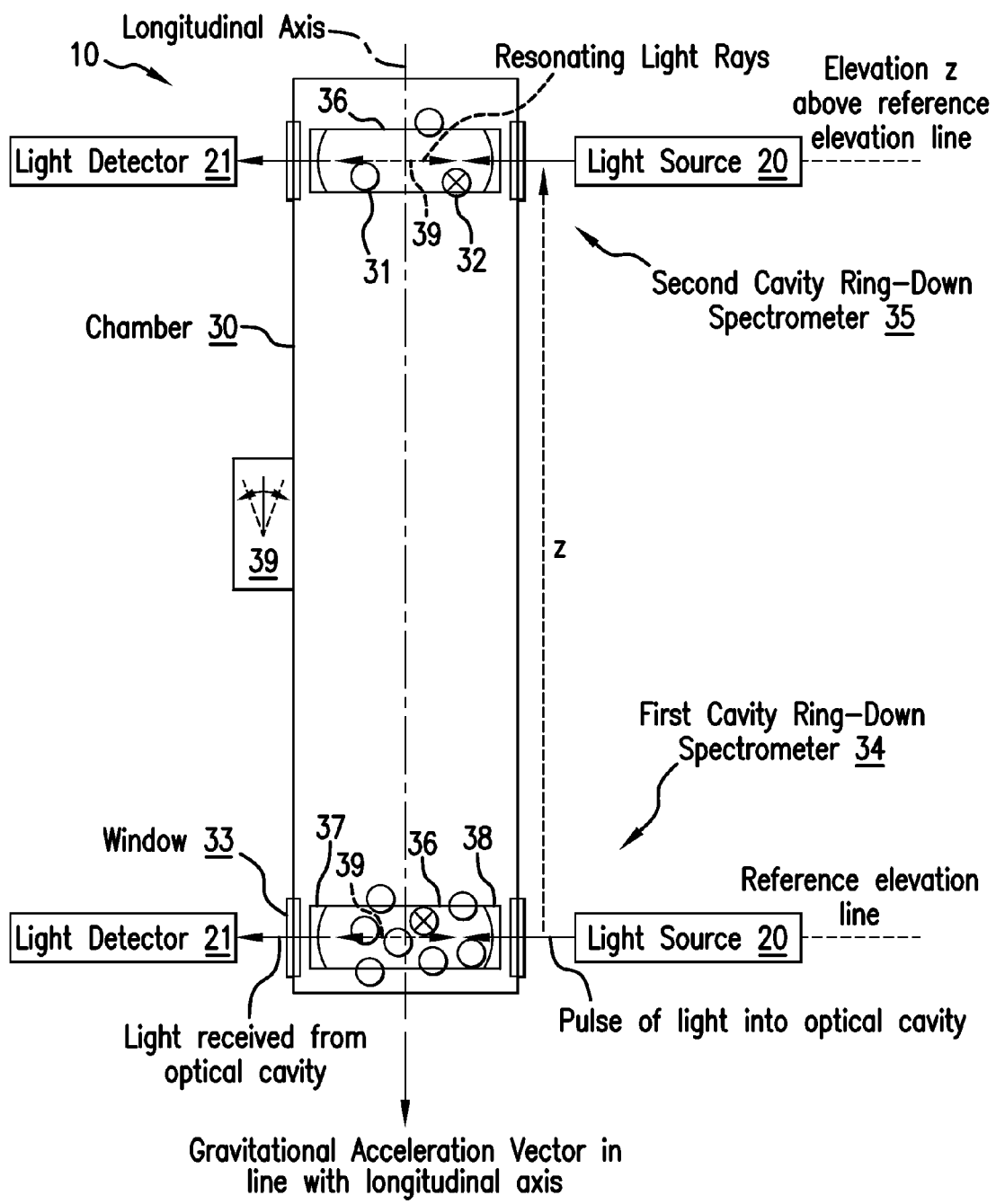
FIG. 3 depicts aspects of the gravimeter.

FIG. 3 depicts aspects of the gravimeter 10. The gravimeter 10 includes a chamber 30 configured to be sealed to contain a first gas 31 and optionally a second gas 32 that is much lighter than the first gas 31. The chamber 30 can be transparent to light (i.e., photons) or in can have one or more windows 33 that can convey light used to interrogate the gases 31 and 32. When the windows 33 are used, the chamber 30 can be fabricated from a strong non-transparent material such as a metal to withstand the rigors of the borehole environment. In addition, a metal chamber 30 has a high thermal conductivity, which is important for keeping the gases 31 and 32 at the same temperature. In one or more embodiments, the windows 33 are made of diamond, which has a high thermal conductivity. Maintaining the gases at the same temperature avoids creating higher densities of the gases in cooler spots in the chamber. In general, an outer housing prevents the chamber from being exposed to high borehole pressures. Shown in FIG. 3 is a longitudinal axis of the chamber 30 for reference. The longitudinal axis may represent any axis in the chamber along which gravitational acceleration or a vector component of gravitational acceleration acts on gas in the chamber.

Still referring to FIG. 3, the gravimeter 10 includes a first cavity ring-down spectrometer (CRDS) 34 located toward the bottom of the chamber 30 and a second cavity ring-down spectrometer 35 located toward the top of the chamber 30. The location of the first CRDS 34 may be considered a reference elevation line, while the location of the second CRDS 35 may be considered an elevation z or height z above the reference elevation line. Each cavity ring-down spectrometer is configured to measure the mole fraction or molar concentration of each gas to determine the density of each gas at the elevation of each spectrometer. The first CRDS 34 includes an optical cavity 36, which in one or more embodiments includes a first mirror 37 and a second mirror 38, although other types of optical cavities may also be used. In one or more embodiments, each mirror is a plano-concave mirror. The optical cavity 36 is configured to allow gases in the chamber 30 to enter it so that resonating light in the optical cavity 36 can be absorbed by those gases. Light rays or an average of the light rays resonating in the optical cavity 36 travel along an optical axis 39.

Still referring to FIG. 3, a light source 20, such as a laser for example, is configured to emit a pulse of light into the optical cavity 36 at a wavelength that is in resonance with the optical cavity 36. In one or more embodiments, the wavelength of photons in the light pulse is at or near an absorption spectrum peak of the first gas 31. In general, the light emitted by a CRDS is in the infrared region in order to interact with the first gas 31 to perform cavity ring-down spectroscopy. The light in the cavity reflects back and forth within the cavity. As the light travels within the cavity, some of the light is attenuated by the first gas 31 that scatters and/or absorbs the light. Some of the light will make many passes through the optical cavity before the light is scattered or absorbed. A light detector 21 (also referred to as a photodetector) measures the intensity of some of the light leaking from the optical cavity. Electronics such as the downhole electronics 7 measures the decay rate of the detected light to determine an exponential decay time constant τ. The exponential decay time constant τ may then be correlated to the molar concentration (i.e., density) of the first gas 31 recognizing that a higher concentration of gas will result in a shorter exponential decay time characterized by the exponential time decay constant, τ. The first CRDS 34 thus provides a first density measurement (D1) of the first gas 31 at the reference elevation. The second CRDS 35 has components the same as or similar to the components of the first CRDS 34 and thus provides a second density measurement (D2) of the first gas 31 at the elevation z or height z above the reference elevation. From the two density measurements, P may be determined as the ratio D2/D1. The temperature T may be sensed by a temperature sensor (not shown) and used as input to Equation 1. By knowing this data and the type of molecule of the first gas 31 and, thus, the mass M of this molecule, the gravitational acceleration can be calculated as discussed above.

To increase the sensitivity and, thus, the accuracy of the gravity measurements, the two cavity ring-down spectrometers 34 and 35 should be located as far apart from each other as practical within the constraints of the gravimeter 10 that are necessary for being conveyed within the confines of the borehole 2. The further apart they are, the greater the difference will be between D1 and D2 resulting in more sensitivity or dynamic range. Similarly, the greater the mass M of the first gas 31, the greater the difference will be between D1 and D2 resulting in more sensitivity or dynamic range. Consequently, in one or more embodiments, the first gas 31 is selected to be perfluorodecalin, which are heavy gas molecules having a molecular weight of 462, a mass of 7.67E-25 kg, and an infrared absorption spectrum peak. Perfluorodecalin is one of the heaviest gas molecules that is also non-toxic and non-corrosive. It has even been used in medicine as artificial blood to carry oxygen and in eye surgery. Being non-toxic is important because the borehole environment can be harsh resulting in damaged equipment. A damaged gravimeter 10 leaking perfluorodecalin will not result in hazardous clean-up costs or a contaminated environment. In addition, the perfluorodecalin can be easily handled without special safety precautions resulting decreased operational costs. A list of 643 different gases was ranked by mole weight and reviewed. The top five and bottom seven gases are shown in Table 1. It can be seen that perfluorodecalin is the third heaviest gas by molecular weight, but also the heaviest gas that is non-toxic. Perfluorodecalin has a boiling point of 142° C. at one atmosphere pressure. Hence, reduced pressure or elevated temperature must be maintained in the chamber for perfluorodecalin to be in the gaseous state. Perfluorodecalin gas is over one and a half times heavier (giving it a 1.55 times greater Boltzmann density gradient) than tungsten hexafluoride gas, which may be used in other sensors, to provide greater sensitivity or dynamic range.

TABLE 1

| RANK | CHEMICAL FORMULA | GAS NAME | MOLE WEIGHT (g/mol) |
|---|---|---|---|
| 1 | I4Ti | Titanium Tetraiodide | 555.52 |
| 2 | I4Si | Silicon Tetraiodide | 535.71 |
| 3 | C10F18 | Perfluorodecalin | 462.07 |
| 4 | AlI3 | Aluminum Triiodide | 407.70 |
| 5 | BI3 | Boron Triiodide | 391.55 |
| ... | ... | ... | ... |
| 637 | CH4 | Methane | 16.04 |
| 638 | T2 | Tritium | 6.32 |
| 639 | D2 | Deuterium (equilibrium) | 4.03 |
| 640 | D2 | Deuterium | 4.03 |
| 641 | He | Helium | 4.00 |
| 642 | HD | Hydrogen Deuteride | 3.02 |
| 643 | H2 | Hydrogen | 2.02 |

It can be appreciated that it may be advantageous to orient the optical cavity 36 such that light rays passing through and/or reflecting within the optical cavity are perpendicular or substantially perpendicular (i.e., output within 10% of reading with perpendicular optical axis) to the longitudinal axis in order to increase the accuracy of the density measurement. In this perpendicular orientation, the light rays at or near an absorption wavelength of the gas molecules will interact with gas molecules that are at the same reference elevation line and, thus, at the same density. This avoids measuring the density of gas molecules at locations other than the reference elevation and elevation z. Of course, in a deviated borehole, the laser's path through the gas will not be along a path of constant elevation, but will follow a path that is partially below and partially above a constant elevation and, only on average, at the elevation z.

As discussed above, the second gas 32 may be included in the container 30. The second gas 32 is selected to be much lighter than the first gas 31. Specifically, the second gas 32 is selected to a have a mass such that a density change of that gas between the reference elevation and the elevation z is minimal (e.g., less than one hundred parts per million in one or more embodiments). Hence, a significant measured density change from a previous density measurement of the second gas 32 can be attributed to a change in volume of the chamber 30 due to thermal expansion or contraction. In one or more embodiments, knowing chamber dimensions and material of a specific chamber, changes in the distance z resulting from a chamber volume change can be determined by analysis or testing for various temperatures of the specific chamber. Accordingly, a significant measured change in the density of the second gas 32 with respect to a previous measurement (e.g., an amount of change above one percent) can be correlated to a specific change in the distance z. Knowing a more accurate z value will result in a more accurate estimate of gravitational acceleration g. In one or more embodiments, the resonance wavelength of the optical cavity 36 is selected to be at or near an absorption peak of the second gas 32 in addition to being near the absorption peak of the first gas 31.

In one or more embodiments, the second gas 32 is methane. Methane is a light gas that has an infrared absorption spectrum peak that enables the density of this gas to be measured by the first CRDS 34 and/or the second CRDS 35. Being light, methane also provides for thermalization (i.e. rapidly exchanging heat to keep temperature T constant) of the first gas 31. Perfluorodecalin has a density gradient that is 28.8 times the density gradient of methane so that perfluorodecalin density changes resulting from gravity changes are significantly greater than methane density changes.

Figure 4:
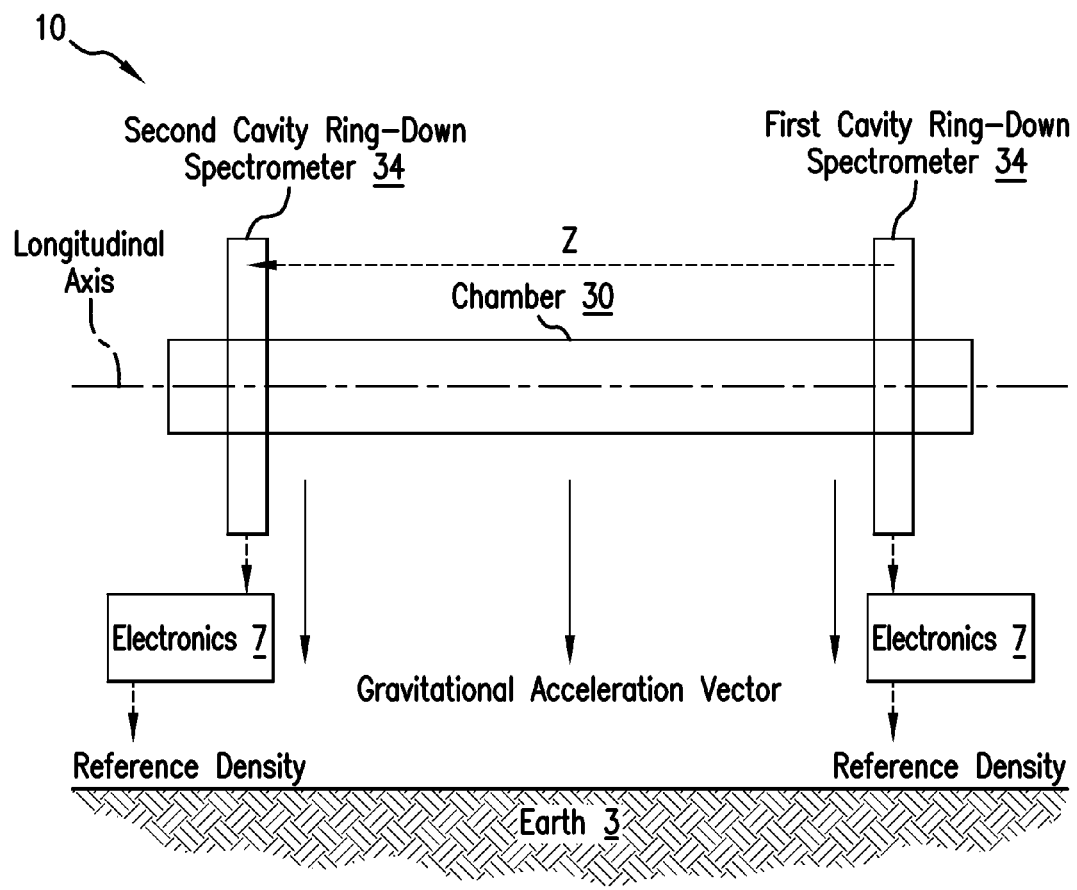
FIG. 4 depicts aspects of an embodiment of a calibration orientation of the gravimeter.

The gravimeter 10 may be operated using several techniques. In a first technique, a density measurement of the first gas 31 (D1) is obtained from one CRDS such as the first CRDS 34. A ratio of density of the first gas (D1) to a reference density (DR) may be calculated. As estimate of gravitational acceleration is then computed from the ratio (DR/D1) and the known molecular weight of the heavier gas. The reference density (DR) in one or more embodiments is obtained from the first CRDS 34 or the second CRDS 35 when the chamber 30 is oriented in a reference orientation (e.g., horizontally) for which the density of the first gas 31 is the same throughout the chamber 30. In one or more embodiments, the reference orientation is when the longitudinal axis of the chamber 30 is horizontal as illustrated in FIG. 4. When the longitudinal axis of the chamber 30 is horizontal, the density of the first gas 31 is the same when measured by the first CRDS 34 or the second CRDS 35. Accordingly, a density measurement with the chamber 30 in the reference orientation provides the reference density measurement. A density measurement for determining gravity is the performed with the chamber in a gravity measurement orientation (e.g., the longitudinal axis of the chamber being vertical or at least non-horizontal and having a vector component in line with gravitational acceleration). The horizontal reference density would be a sufficient reference density if the chamber dimensions did not change with temperature. To account for thermal expansion of the chamber itself, a density measurement of the second gas 32 may also be performed and used as another reference density. In that the second gas 32 is much lighter than the first gas 31, very little measured density change of the second gas 32 resulting from gravity change is expected. Hence, a change in this other reference density, if any, above a threshold is used to indicate whether the distance z, between the first and second CRDSs, has changed. If a change in z above a threshold is detected, then a correction factor can be applied to the gravity estimate.

In another technique, density measurements of the first gas 31 are obtained using the first CRDS 34 and the second CRDS 35 to provide a first density measurement (D1) and a second density measurement (D2), respectively. As discussed above, gravitational acceleration may then be determined by solving Equation (1) for gravitational acceleration g where P is D2/D1. In addition, a density measurement of the second (lighter) gas 32 may be obtained using the first CRDS 34 and/or the second CRDS 35 in order to obtain a temperature-corrected value of the distance z for use in Equation (1).

It can be appreciated that the gravimeter 10 may be used in boreholes that are deviated from the vertical. In one or more embodiments, an inclinometer 39 (as shown in FIG. 3) may be coupled to the chamber 30 in order to measure an amount of inclination from the vertical of the chamber 30. By knowing the amount of inclination, the vector component of the gravitational acceleration causing a density difference of the first gas 31 may be calculated. Further, the total gravitational acceleration at the gravimeter 10 may be calculated from the gravitational acceleration vector component using vector algebra. In an alternative embodiment, the gravimeter 10 may include three sets of chambers 30, first CRDSs 34, and second CRDSs 35 oriented at various angles to each other to measure the gravitational vector components in three orthogonal directions. The vector sum of the three orthogonal components then provides the total gravitational acceleration at the gravimeter 10.

It can be appreciated that the light source 20 may be tunable to emit light at two or more desired wavelengths in order to measure the density of the first gas 31 and the second gas 32. In one or more embodiments, the density measurements of the gases 31 and 32 can alternate back and forth from the absorption spectral peak of one gas to the spectral peak of the other gas so as to compare their relative concentrations based on their relative absorbances. In the embodiment where the first gas 31 is perfluorodecalin and the second gas 32 is methane, the infrared spectral peaks are both close to approximately 8 eight microns in wavelength and can allow for a high rate of alternating measurements by rapidly tuning the laser from one wavelength that is best absorbed by the first gas 31 to the another nearby wavelength that is best absorbed by the second gas 32.

It can be appreciated that a gravity gradient may be required to determine certain downhole information such as hydrocarbon concentrations. The gravity gradient may be determined by performing gravitational acceleration measurement with the gravimeter 10 at a plurality of depths in the borehole 2.

Figure 5:
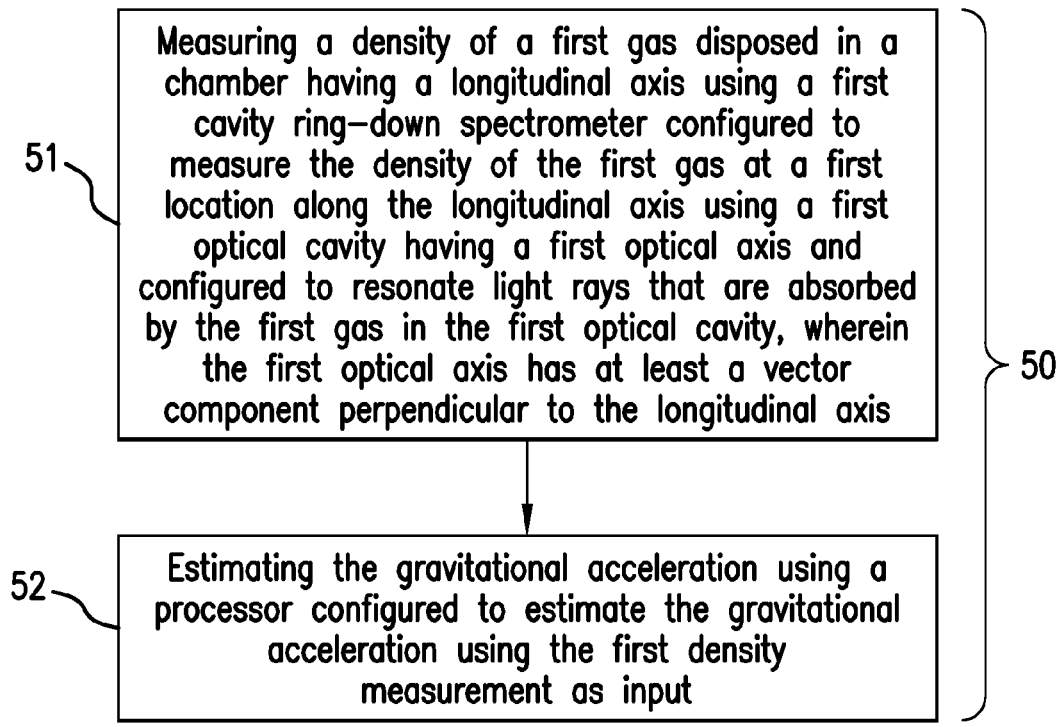
FIG. 5 is a flow chart depicting a method for determining gravitational acceleration with the gravimeter.

FIG. 5 is a flow chart of an exemplary method 50 for estimating gravitational acceleration. Block 51 calls for measuring a density of a first gas disposed in a chamber having a longitudinal axis using a first cavity ring-down spectrometer configured to measure the density of the first gas at a first location along the longitudinal axis using a first optical cavity having a first optical axis and configured to resonate light rays that are absorbed by the first gas in the first optical cavity. The first optical axis has at least a vector component perpendicular to the longitudinal axis. Block 52 calls for estimating the gravitational acceleration using a processor configured to estimate the gravitational acceleration using the first density measurement as input. Further, the method 50 may also include measuring a density of the first gas at a second location along the longitudinal axis using a second cavity ring-down spectrometer to provide a second density measurement and estimating the gravitational acceleration using a ratio of the second density measurement to the first density measurement. Further, the method 50 may also include measuring a density of a second gas disposed in the chamber, the second gas being lighter than the first gas, determining a change in volume of the chamber using the density of the second gas, and estimating the gravitational acceleration using the determined change in volume of the chamber. Further, the method 50 may also include determining a reference density of the first gas by measuring a density of the first gas when a longitudinal axis of the chamber is horizontal such that the density does not vary along the axis.

It can be appreciated that the cavity ring-down spectrometer (CRDS) provides several advantages. The CRDS is a highly sensitive spectrometer that can provide higher accuracy than other spectrometers, which is necessary for making gravitational acceleration measurements where differences in gas density measurements may be very small. In addition, the length of the chamber and, thus, the distance z between CRDS's may be constrained due to the necessity of being able to be conveyed through the borehole. A smaller distance z may further lead to smaller differences in gas density measurements requiring highly sensitive gas density measurements. In one or more embodiments, the CRDS can measure molar fractions down to the parts per trillion level.

In support of the teachings herein, various analysis components may be used, including a digital and/or an analog system. For example, the downhole electronics 7, the surface computer processing 8, the first CRDS 34, the second CRDS 35, and/or the inclinometer 39 may include the digital and/or analog system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, vacuum pump, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottomhole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or any combination of terms. The terms "first" and "second" are used to distinguish elements and are not used to denote a particular order. The term "couple" relates to coupling a first component to a second component either directly or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating gravitational acceleration, the apparatus comprising:
a chamber configured to contain a first gas, the chamber having a longitudinal axis;
a first cavity ring-down spectrometer configured to measure a density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis;
a second gas contained in the chamber, the second gas being lighter than the first gas, wherein the first cavity ring-down spectrometer is further configured to measure a density of the second gas at the first location; and
a processor configured to receive a first density measurement from the first cavity ring-down spectrometer and to estimate the gravitational acceleration using the first density measurement, wherein the processor is further configured to calculate a change in volume of the chamber using a density measurement of the second gas.

2. The apparatus according to claim 1, wherein the processor is further configured to determine a ratio of a reference density to the first density measurement to estimate the gravitational acceleration.

3. The apparatus according to claim 2, wherein the reference density is a density of the first gas measured when the chamber is oriented in a reference orientation such that density measurements at different locations in the chamber provide the same values.

4. The apparatus according to claim 3, wherein the longitudinal axis is horizontal in the reference orientation.

5. The apparatus according to claim 1, further comprising:
a carrier configured to be conveyed through a borehole penetrating the earth.

6. The apparatus according to claim 5, wherein the carrier comprises a wireline, a slickline, a drillstring, or coiled tubing.

7. The apparatus according to claim 5, further comprising an inclinometer configured to measure deviation of the longitudinal axis of the chamber from a vertical orientation.

8. The apparatus according to claim 1, wherein the first gas is perfluorodecalin.

9. The apparatus according to claim 1, wherein the processor is further configured to estimate the gravitational acceleration using the calculated change in volume of the chamber.

10. The apparatus according to claim 1, wherein the chamber comprises a window transparent to light entering the optical cavity or light leaving the optical cavity.

11. The apparatus according to claim 1, wherein the first optical axis is substantially perpendicular to the longitudinal axis.

12. The apparatus according to claim 1, wherein the first optical axis is perpendicular to the longitudinal axis.

13. An apparatus for estimating gravitational acceleration, the apparatus comprising:
a chamber configured to contain a first gas, the chamber having a longitudinal axis;
a first cavity ring-down spectrometer configured to measure a density of the first gas at a first location along the longitudinal using a first optical cavity having a first optical axis and configured to resonate light rays that are absorbed by the first gas in the first optical cavity, wherein the first optical axis has at least a vector component perpendicular to the longitudinal axis;
a processor configured to receive a first density measurement from the first cavity ring-down spectrometer and to estimate the gravitational acceleration using the first density measurement;
a second cavity ring-down spectrometer configured to measure a density of the first gas at a second location along the longitudinal axis using a second optical cavity having a second optical axis and configured to resonate light rays that are absorbed by the first gas in the second optical cavity, wherein the second optical axis has at least a vector component perpendicular to the longitudinal axis, and wherein the processor is further configured to receive a second density measurement from the second cavity ring-down spectrometer and to estimate the gravitational acceleration using the second density measurement, wherein the processor is further configured to calculate a ratio of the second density measurement to the first density measurement to estimate the gravitational acceleration;
a second gas contained in the chamber, the second gas being lighter than the first gas, wherein the first cavity ring-down spectrometer is further configured to measure a density of the second gas at the first location, the second cavity ring-down spectrometer is further configured to measure a density of the second gas at the second location, and the processor is further configured to calculate a change in volume of the chamber using density measurements of the second gas obtained from the first and second cavity ring-down spectrometers.

14. The apparatus according to claim 13, wherein the processor is further configured to estimate the gravitational acceleration using the calculated change in volume of the chamber.

15. The apparatus according to claim 13, wherein the second gas is methane.

16. A method for estimating gravitational acceleration, the method comprising:
measuring a density of a first gas disposed in a chamber having a longitudinal axis using a first cavity ring-down spectrometer configured to measure the density of the first gas at a first location along the longitudinal axis using a first optical cavity having a first optical axis and configured to resonate light rays that are absorbed by the first gas in the first optical cavity, wherein the first optical axis has at least a vector component perpendicular to the longitudinal axis;
estimating the gravitational acceleration using a processor configured to estimate the gravitational acceleration using the first density measurement as input;
measuring a density of a second as disposed in the chamber, the second gas being lighter than the first gas;
calculating a change in volume of the chamber using the density of the second gas; and
estimating the gravitational acceleration using the calculated change in volume of the chamber.

17. The method according to claim 16, further comprising determining a ratio of a reference density to the first density measurement to estimate the gravitational acceleration.

18. The method according to claim 17, further comprising determining the reference density by measuring a density of the first gas when the longitudinal axis of the chamber is horizontal.

19. The method according to claim 16 further comprising measuring a density of the first gas at a second location along the longitudinal axis using a second cavity ring-down spectrometer to provide a second density measurement and estimating the gravitational acceleration using a ratio of the second density measurement to the first density measurement, the second ring-down spectrometer comprising a second optical cavity having a second optical axis and configured to resonate light rays that are absorbed by the first gas in the second optical cavity, wherein the second optical axis has at least a vector component perpendicular to the longitudinal axis.

20. The method according to claim 19, further comprising measuring a density of a second gas at the first location using the first cavity ring-down spectrometer, the second gas being lighter than the first gas, measuring a density of the second gas at the second location using the second cavity ring-down spectrometer, calculating a change in volume of the chamber from the density measurements of the second gas, and estimating the gravitational acceleration using the calculated change in volume of the chamber.

21. The method according to claim 16, wherein the first gas is perfluorodecalin.

22. The method according to claim 16, wherein the second gas is methane.

* * * * *